(12) United States Patent
Seward et al.

(10) Patent No.: US 8,016,786 B2
(45) Date of Patent: Sep. 13, 2011

(54) DUAL MODULUS BALLOON FOR INTERVENTIONAL PROCEDURES

(75) Inventors: Kirk Patrick Seward, San Francisco, CA (US); Isidro M. Gandionco, Fremont, CA (US); David Gandionco, Fremont, CA (US)

(73) Assignee: Mercator MedSystems, Inc., San Leandro, CA (US)

( * ) Notice: Subject to any disclaimer, the term of this patent is extended or adjusted under 35 U.S.C. 154(b) by 18 days.

(21) Appl. No.: 12/711,141

(22) Filed: Feb. 23, 2010

(65) Prior Publication Data

US 2010/0145307 A1 Jun. 10, 2010

Related U.S. Application Data

(62) Division of application No. 11/858,797, filed on Sep. 20, 2007, now Pat. No. 7,691,080.

(60) Provisional application No. 60/826,478, filed on Sep. 21, 2006.

(51) Int. Cl.
*A61M 25/10* (2006.01)

(52) U.S. Cl. ........... 604/96.01; 604/103.07; 604/103.08; 606/192

(58) Field of Classification Search .................. 604/272, 604/103.01, 103.02, 103.07, 103.08, 96.01; 606/185, 190–192, 194–195, 159, 167, 170
See application file for complete search history.

(56) References Cited

U.S. PATENT DOCUMENTS

| | | | |
|---|---|---|---|
| 5,009,659 A | 4/1991 | Hamlin et al. | |
| 5,078,725 A | 1/1992 | Enderle et al. | |
| 5,196,024 A | 3/1993 | Barath | |
| 5,562,620 A * | 10/1996 | Klein et al. | 604/103.01 |
| 5,681,281 A | 10/1997 | Vigil et al. | |
| 5,749,851 A | 5/1998 | Wang | |
| 6,102,904 A | 8/2000 | Vigil et al. | |
| 6,210,392 B1 * | 4/2001 | Vigil et al. | 604/507 |
| 6,527,741 B1 | 3/2003 | Lee et al. | |
| 6,547,803 B2 * | 4/2003 | Seward et al. | 606/185 |
| 6,860,867 B2 | 3/2005 | Seward et al. | |
| 6,872,215 B2 | 3/2005 | Crocker et al. | |

(Continued)

FOREIGN PATENT DOCUMENTS

WO    WO 01/12255    2/2001

OTHER PUBLICATIONS

Supplementary Search Report and Search Opinion of EP Application No. 07842965.1, mailed Nov. 20, 2009, 6 pages total.

(Continued)

*Primary Examiner* — Nicholas D Lucchesi
*Assistant Examiner* — Quynh-Nhu H Vu
(74) *Attorney, Agent, or Firm* — Wilson Sonsini Goodrich & Rosati

(57) ABSTRACT

A device for interventional surgical or medical procedures is presented. The device is generally in the form of a balloon and is used to position itself or other working elements up against or through lumen walls in the body. The balloon is comprised of at least two materials of different elastic modulus, which allows for a flexible but relatively non-distensible, unfolding component of the balloon as well as an elastomeric, inflatable component of the balloon. The elastomeric component is fixedly attached to the flexible but relatively non-distensible component and together they form a pressure vessel that can be inflated within the lumens of the body.

5 Claims, 10 Drawing Sheets

U.S. PATENT DOCUMENTS

| | | |
|---|---|---|
| 7,141,041 B2 | 11/2006 | Seward |
| 7,338,463 B2 | 3/2008 | Vigil |
| 7,413,558 B2 * | 8/2008 | Kelley et al. ............. 604/103.08 |
| 7,691,080 B2 * | 4/2010 | Seward et al. ............. 604/96.01 |
| 2002/0072755 A1 | 6/2002 | Bigus et al. |
| 2002/0188310 A1 | 12/2002 | Seward et al. |
| 2003/0055400 A1 | 3/2003 | Seward et al. |
| 2003/0055446 A1 | 3/2003 | Seward et al. |
| 2003/0171734 A1 | 9/2003 | Seward et al. |
| 2005/0033225 A1 | 2/2005 | Wu et al. |
| 2005/0137617 A1 * | 6/2005 | Kelley et al. .................. 606/170 |

OTHER PUBLICATIONS

International Search Report and Written Opinion of PCT Application No. PCT/US07/79163, dated Sep. 15, 2008, 6 pages total.

* cited by examiner

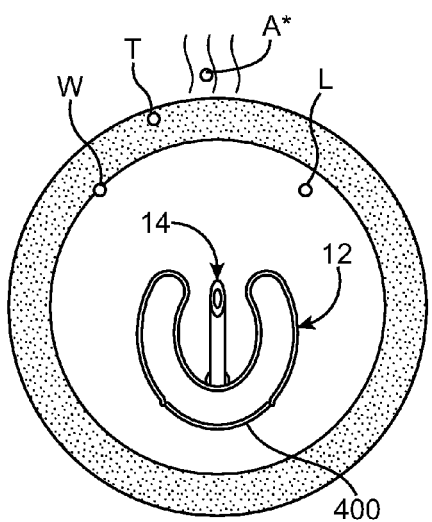 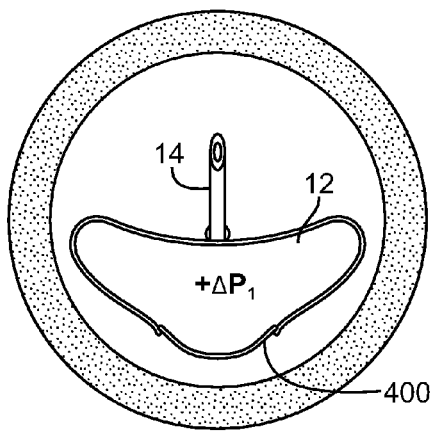
FIG. 10A  FIG. 10B
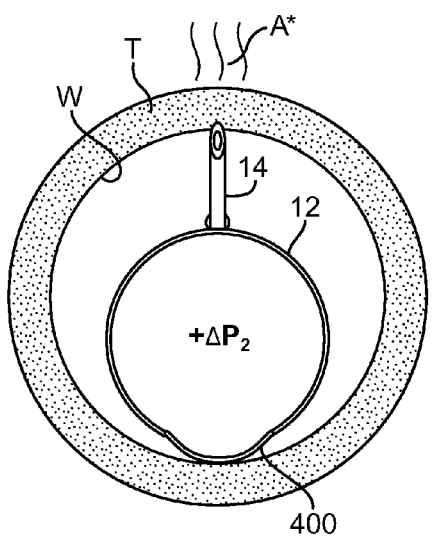 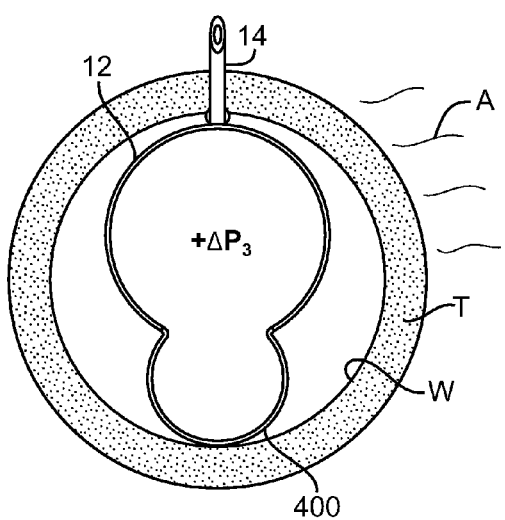
FIG. 10C  FIG. 10D

DUAL MODULUS BALLOON FOR INTERVENTIONAL PROCEDURES

CROSS-REFERENCES TO RELATED APPLICATIONS

The present application is a divisional of U.S. application Ser. No. 11/858,797, filed on Sep. 20, 2007, which claims the benefit of provisional U.S. application Ser. No. 60/826,478, filed on Sep. 21, 2006, the full disclosures of which are incorporated herein by reference.

BACKGROUND OF THE INVENTION

1. Field of the Invention

The present invention relates generally to medical methods and devices. More particularly, the present invention relates to intraluminal catheters with balloons having segments with different material moduli, which upon inflation improve apposition of tools against luminal structures, such as blood vessel walls or walls of other body lumens such as bronchi or the urethra.

Coronary artery disease is the leading cause of death and morbidity in the United States and other Western societies. In particular, atherosclerosis in the coronary arteries can cause myocardial infarction, commonly referred to as a heart attack, which can be immediately fatal or, even if survived, can cause damage to the heart which can incapacitate the patient. Other coronary diseases which cause death and incapacitation include congestive heart failure, vulnerable or unstable plaque, and cardiac arrhythmias. In addition to coronary artery disease, diseases of the peripheral vasculature can also be fatal or incapacitating. Vascular occlusions, blood clots and thrombus may occlude peripheral blood flow, leading to tissue and organ necrosis. Deep vein thrombosis in the legs can, in the worst cases, require amputation. Clots in the carotid artery can embolize and travel to the brain, potentially causing ischemic stroke. Diseases causing narrowing of a lumen in the body are not limited to blood vessels. As examples, but by no means limiting, chronic obstructive pulmonary disease (COPD) and cancerous tumors may cause constriction of bronchi in the lungs, and prostate cancer or benign prostatic hyperplasia (BPH) may cause constriction of the urethra.

Percutaneous or endoscopic interventional procedures are very common in the United States and other countries around the world. Intravascular catheter systems are used for procedures such as balloon angioplasty, stent placement, atherectomy, retrieval of blood clots, photodynamic therapy, and drug delivery. All of these procedures involve the placement of long, slender tubes known as catheters into arteries, veins, or other lumens of the body in order to provide access to the deep recesses of the body without the necessity of open surgery.

Percutaneous procedures also include those that place working ends of catheters into body cavities such as the ventricles or atria of the heart. The placement of needles into the heart wall from within a ventricle can also be performed during catheter-based procedures as described in the previous paragraph.

Medical devices used in catheter procedures often include a working component at or near the distal (farthest from the operator) end of the catheter that is operated by hydraulic, pneumatic, or other mechanical means. These systems can sometimes include a working component such as a microneedle on one side of the catheter or at the distal end of the catheter that must be apposed against the wall of the lumen.

Such catheters can also benefit the treatment of other lumens in the body. For example, the sinus passages leading from nasal openings to the sinuses or pharynx may become inflamed, for example after sinus surgery or in the case of nasal polyposis. In these cases, systems similar to those used in percutaneous procedures may also require apposition of one side of the working end against the lumen wall.

Of particular interest to the present invention, catheters carrying microneedles capable of delivering therapeutic and other agents deep into the adventitial layer surrounding blood vessel lumens have been described U.S. Pat. No. 6,547,803, issued on Apr. 15, 2003, and in co-pending application Ser. Nos. 09/961,080, filed on Sep. 20, 2001, and 09/961,079, also filed on Sep. 20, 2001, all of which have common inventorship with but different assignment than the present application, the full disclosures of which are incorporated herein by reference.

The designs described in the issued patent and copending applications have numerous advantages. The microneedles are delivered in a direction which is substantially perpendicular to the axis of the catheter, thus maximizing the depth of needle penetration into the wall and reducing trauma and injury. Moreover, by locating the needles on the exterior of an expanding involuted surface, the needles can be injected into tissue fully up to their point of attachment to the catheter, further maximizing the needle penetration depth which may be achieved.

Such deep needle penetration depends at least partly, however, on having an expansible surface structure chosen to accommodate the size of the lumen being treated. As lumen sizes may vary significantly, it may be necessary to maintain an inventory of differently sized catheters to address all patients and conditions.

While functional, the need to maintain and manufacture an inventory of catheters with differently sized balloons is costly. Moreover, should the physician choose the wrong balloon for a procedure, it may become necessary to replace the balloon with a second balloon catheter, further increasing the cost and time necessary to perform the procedure.

For these reasons, it would be desirable to provide improved devices and methods for transmitting appositional force from one side of a catheter-based balloon to the other opposite side. In particular, it would be desirable to provide intravascular and other intraluminal catheters having balloons or other inflation structures for advancing needles and other tools toward or into adjacent luminal walls, where the inflation structures are selectively inflatable to different sizes in order to accommodate different luminal diameters and/or to penetrate needles to different depths. Preferably, such selective inflation would be accomplished by delivering different pressures or volumes of inflation media to the inflatable structures. It is a further objective that the methods be simple and economic to implement and be useful with a wide range of vascular and other medical catheters. At least some of these objectives will be met by the inventions described hereinafter.

2. Description of the Background Art

Catheters used to slide microneedles through vessel walls are described in U.S. Pat. No. 6,547,803, issued on Apr. 15, 2003, and in co-pending application Ser. Nos. 09/961,080, filed on Sep. 20, 2001, and 09/961,079, also filed on Sep. 20, 2001, all of which have common inventorship with but different assignment than the present application, the full disclosures of which are incorporated herein by reference.

BRIEF SUMMARY OF THE INVENTION

The present invention provides catheters with a single balloon or other inflatable actuator which is inflated at a first pressure to unfurl or deploy a first portion of the balloon, where delivery of an additional inflation pressure or volume expands or otherwise deploys a second portion of the balloon wall to a size larger than or a configuration different than that achievable by inflation or unfurling of the first portion of the balloon wall alone. Multiple components may be combined into the same balloon or pressure component, such that one part of the wall is non-distensible and another part of the wall is compliant or elastomeric, such that a single inflation step, whether it involves volume or pressure, may be useful to activate both the non-distensible and compliant structures simultaneously or in series.

The present invention also provides catheters and methods for deploying interventional tools in blood vessels and other body lumens. The interventional tools are typically needles which are penetrated into a luminal wall, but could be other structures such as atherectomy blades, optical fibers for delivering laser energy, mechanical abrasion and drilling components, and the like. The catheters comprise a catheter body having a proximal end and a distal end. The needle or other interventional tool is coupled to a distal portion of the catheter, and an inflatable structure is provided on or near the distal portion of the catheter body in order to advance the tool laterally relative to an axis of the catheter body. The inflatable structure may comprise two or more discrete regions which deform or inflate at different, typically successive inflation pressures. Usually, the regions will have different elasticities (where one may be substantially non-elastic or non-distensible), but in certain embodiments the regions could have identical elasticities where inflation of one or more of the regions below threshold pressure is prevented by tethers or other restraints which yield or break above said threshold pressure(s). By providing at least one non-distensible region, the non-distensible region can be fully inflated at relatively low pressures to a preselected size. If additional force or lateral displacement is needed, the inflatable structure can then be inflated beyond the first inflation threshold in order to expand one or more additional regions of the balloon, where the additional regions may have the same inflation characteristics or different inflation characteristics.

The regions of differing elasticity in the inflation structure can be achieved and fabricated in a variety of ways. In the exemplary embodiments below, the regions are formed in an edge-to-edge manner or along an overlapping border region using conventional masking and deposition techniques. It will be appreciated that the regions could also be formed by layering materials of differing elasticities, providing layers having different thicknesses, providing reinforcement fibers or materials which create regions of different elasticity within a matrix of the same material, providing tethers and other stretchable or breakable elements within regions of the inflation structure which yield or break when tension is applied above threshold levels, and the like.

The interventional tool may be mounted directly on the catheter body, but in the illustrated embodiments is mounted on the inflatable structure itself. It will be appreciated that more than one interventional tool may be mounted on the catheter, and that such multiple tools may be mounted directly on the catheter body, on the inflatable structure, or both.

By "non-distensible," it is meant that the material of the balloon will be inflatable from a lower profile or volume configuration to an expanded or higher profile or volume configuration. Once at the higher volume, expanded configuration, however, the material will no longer stretch or expand to any reasonable extent (typically less than 200% elongation in any direction prior to rupture) even though the inflation pressure can be raised significantly above the threshold pressure which achieves the higher volume inflation. By "elastomeric" it is meant that the material displays elasticity as more pressure is applied. Usually, there will be minimum or nominal stretching or expansion at or below the threshold pressure, but significant stretching and expansion at inflation pressures above the threshold pressure (typically at least 50% elongation in any direction prior to rupture, often at least 300% elongation in any direction prior to rupture, and usually at least greater than the elongation achievable by the non-distensible material prior to rupture). Additionally, the elastomeric materials will continue to stretch, usually in a nonlinear manner as pressure is increased above the threshold level.

The present invention further provides methods for treating body lumens comprising introducing one or more interventional tools to the body lumen. An inflatable structure is inflated to a first pressure below a threshold pressure to advance the tool laterally to a first "maximum" distance which will not be exceeded so long as the pressure is maintained below the threshold pressure level. After inflation to the first pressure, if it is desired to further laterally advance the intervention tool, the inflatable structure may be inflated to a pressure which exceeds the first threshold pressure to further laterally advance the tool beyond the first maximum distance. The tool may be advanced to a second maximum distance, or alternatively may be incrementally advanced if the inflatable structure includes an elastic region which expands in linear or nonlinear proportion to the inflation pressure.

In a first aspect of the present invention, a medical device comprises a tubular member with a proximal and distal end, an involuted balloon at or near the distal end of the medical device with a working component embedded in the involuted segment, an ability to inflate the involuted balloon to deploy the working component, and a material with lower modulus than the involuted balloon material, affixed to and comprising part of the wall of the involuted structure, such that the lower modulus material may expand at a different rate and create an anchoring or opposing force to the working component. The material with lower modulus may be affixed in one or more ways to the material with higher modulus. In most cases, the lower modulus material resembles a "patch", or membrane structure, on the opposite side of the involuted structure from the working component.

In a second aspect of the present invention similar to the first aspect, the medical device comprises a tubular member with proximal and distal end, a working component at the distal end, and the requirement to place such working component asymmetrically against the wall of a body lumen. The attachment of the lower modulus "patch" to one side of the working component end structure allows for the asymmetric deployment of the working component via hydraulic or pneumatic pressurization of the lower modulus patch, or membrane, with respect to the higher modulus flexible but relatively non-distensible structure to which it is attached.

In a third aspect of the present invention, the working end of the tubular medical device may require particular positioning within a body lumen. Multiple low-modulus "patch", or membrane, structures may be affixed to a higher modulus structure such that the patches may be inflated individually or simultaneously in order to position the tip of the medical device appropriately within the body lumen.

In a fourth aspect of the present invention, the lower modulus "patch" or membrane structure and the higher modulus flexible but relatively non-distensible "anchor" structure meet at a joint that is formed between and consists only of the two materials constituting the patch and the anchor, respectively. The seal formed between the two materials at this joint is free from leakage below a particular amount of pressurization, and thus integrates the two materials to form one pressure vessel with wall components comprised of each material.

In an exemplary embodiment, the low-modulus material (the patch) is a flexible material such as silicone rubber or polydimethylsiloxane (PDMS). The high-modulus material (which can form the anchor to the patch or membrane) is a more flexible but relatively non-distensible polymer such as poly-paraxylylene (parylene N, C, or D). The low modulus material may be generally in a round and flat configuration, but may have more complex shape. The high modulus material is designed to have a "hole" in it approximately the size of the patch material, with some overlap to accommodate the attachment joint. The silicone patch, or membrane, and parylene flexible but relatively non-distensible material may be fixedly attached by polymeric encapsulation or polymeric adhesion, a process in which the parylene is vapor-deposited directly onto three substrates at once: a removable mold material adjacent to the silicone patch, the edge or border region of the silicone patch, and a removable (masking) material that protects the remainder of the silicone patch from being coated. When both removable materials are removed (e.g. by dissolution), the remaining structure is a parylene substrate with an affixed silicone patch, in which the joint formed between the two component structures consists only of the two constituent materials that comprise the individual components.

In the embodiment described above, the silicone patch may be on the back side of a folded balloon structure. The folded balloon structure is primarily comprised of parylene, but the patch comprises at least some of the surface area of the balloon. When the balloon is inflated, the flexible but relatively non-distensible structure unfolds, and then the elastomeric silicone expands due to pressurization. The flexible but relatively non-distensible parylene material unravels, but stretches much less than the silicone, thus forming the dual modulus balloon.

In a further embodiment of the present invention, polymer vapor deposition may be used to form both the flexible but relatively non-distensible material component and a joint or interfacial region between the flexible component and the elastomeric component. Polymer vapor deposition of parylene or other suitable polymer typically begins with sublimation of a parylene dimer or other precursor at an elevated temperature in a low pressure chamber. The dimer vapor is then cleaved into monomer vapor as it travels through a higher temperature furnace. The monomer vapor travels into a deposition chamber, also held under vacuum, but at ambient temperature, at which point the monomer molecules rapidly lose energy and polymerize on surfaces within the deposition chamber. This process creates parylene coatings on components placed into the deposition chamber. Parylene coatings are usually nearly uniform, but thickness of the films varies based on the thermal properties of the system, the amount of dimer used, the intricacy of geometric surfaces placed into the deposition chamber, and the pressure at which the coating process is performed. By properly masking and creating layers, as described hereinafter, the flexible component and the elastomeric component may be joined as the flexible component is being formed. Other variables of the coating process also add to variance in the parylene coating characteristics.

In further exemplary embodiments, the lower-modulus material may be polyether block amide (Pebax), neoprene, Silastic®, chronoprene, C-flex, latex or other elastomeric materials.

In further exemplary embodiments, the higher-modulus material may be a thermoplastic polymer such as polyimide, polyethylene, polypropylene, polyethyl teraphthalate (PET), PTFE (Teflon©), PEEK, Tygon, nylon, acetal or other materials, including polymers, semiconductors, or metals, typically employed in the manufacture of medical devices and products.

In further exemplary embodiments, the attachment joint between the low modulus and high modulus material may be formed by polymer fusion at high temperature or pressure, by the use of adhesives such as cyanoacrylate, or by techniques employing surface preparation by electron bombardment of both materials and then placement of the materials in contact with each other. All of the above may be used to form leak-free seal joints between the low modulus and high modulus materials.

BRIEF DESCRIPTION OF THE DRAWINGS

FIGS. 10A-10D are cross-sectional views of the inflation process of an intraluminal injection catheter useful in the methods of the present invention.

DETAILED DESCRIPTION OF THE INVENTION

By way of example, the first eight figures illustrate a needle injection catheter that can benefit from the dual modulus balloon offered by the present invention.

Figure 1A:
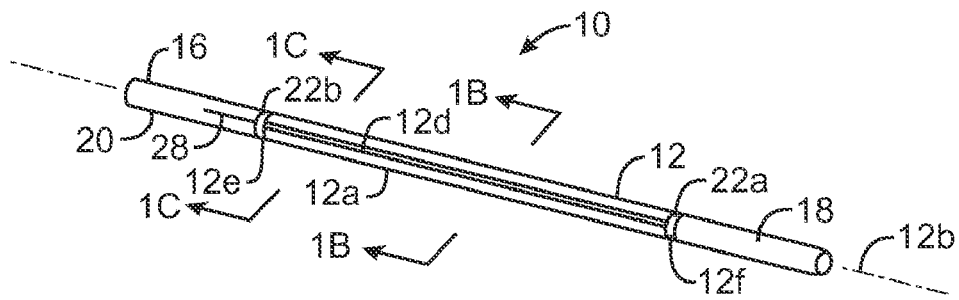
FIG. 1A is a schematic, perspective view of an intraluminal injection catheter suitable for use in the methods and systems of the present invention.
Figure 1B:
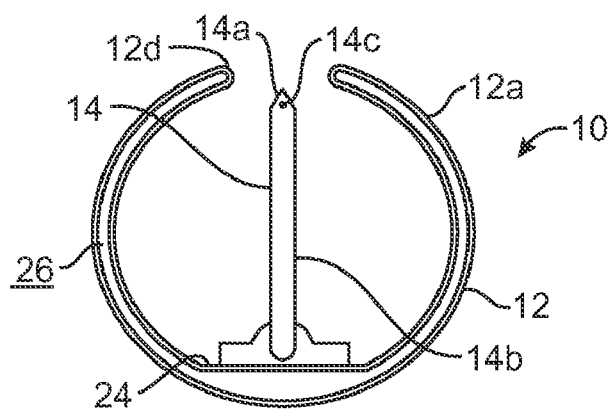
FIG. 1B is a cross-sectional view along line 1B-1B of FIG. 1A.
Figure 1C:
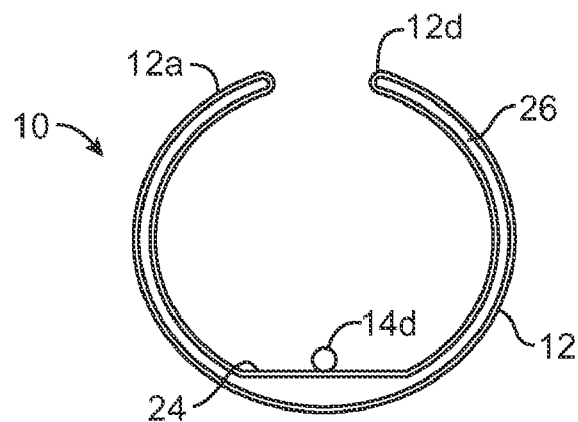
FIG. 1C is a cross-sectional view along line 1C-1C of FIG. 1A.
Figure 2A:
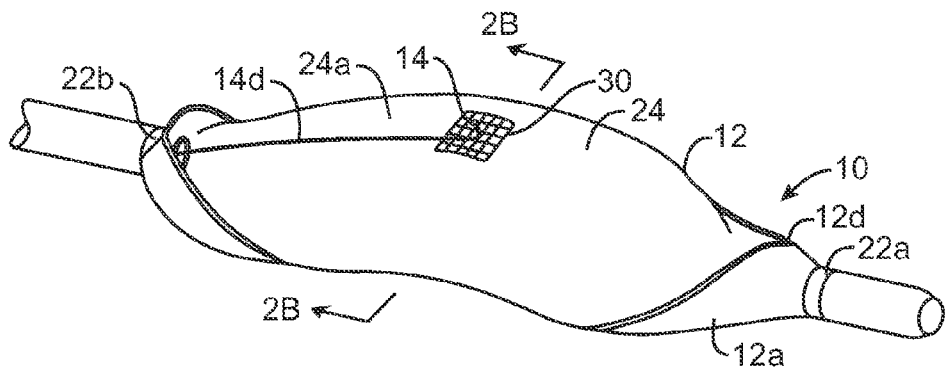
FIG. 2A is a schematic, perspective view of the catheter of FIGS. 1A-1C shown with the injection needle deployed.
Figure 2B:
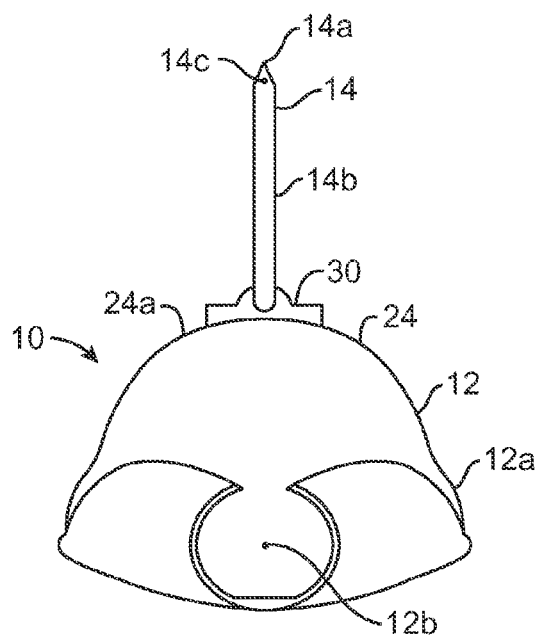
FIG. 2B is a cross-sectional view along line 2B-2B of FIG. 2A.

As shown in FIGS. 1A-2B, a microfabricated intraluminal catheter 10 includes an actuator 12 having an actuator body 12a and central longitudinal axis 12b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially flexible but relatively non-distensible material, such as Parylene (types C, D or N), or a metal, for example, aluminum, stainless steel, gold, titanium or tungsten. The retaining rings form a flexible but relatively non-distensible substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 4), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", assigned to the assignee of the subject application, the entire disclosure of which is incorporated herein by reference.

Figure 3:
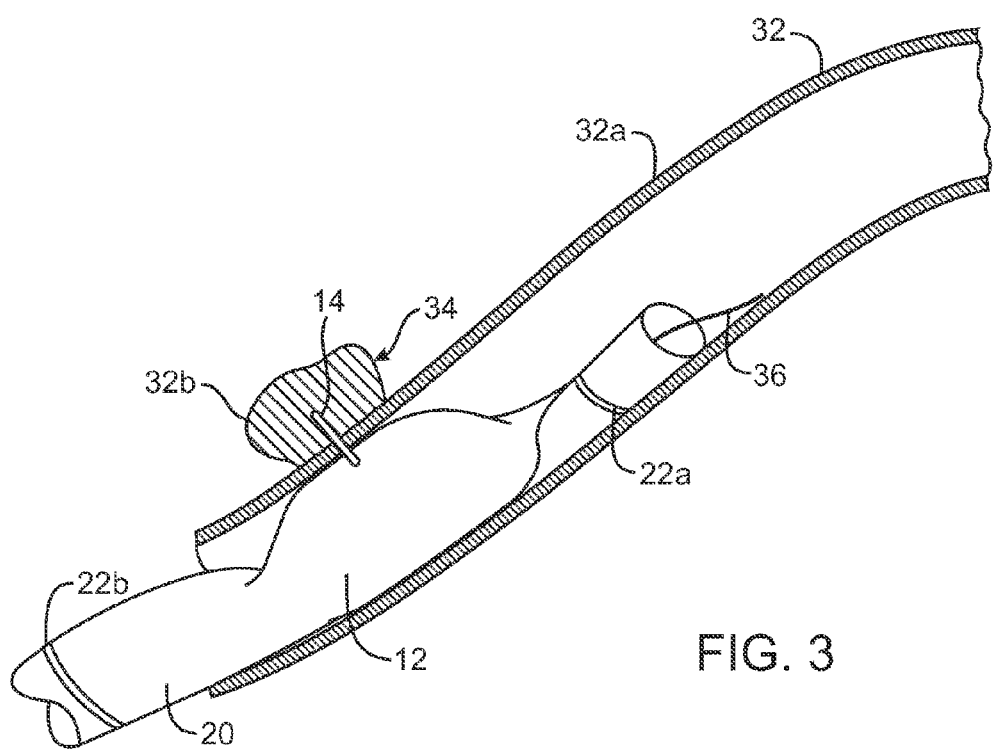
FIG. 3 is a schematic, perspective view of the intraluminal catheter of FIGS. 1A-1C injecting therapeutic agents into an adventitial space surrounding a body lumen in accordance with the methods of the present invention.

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 may be the site of tissue damage or more usually will be adjacent the sites typically being within 100 mm or less to allow migration of the therapeutic or diagnostic agent. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a body lumen wall 32a. It may take only between approximately 100 milliseconds and five seconds for the microneedle to move from its furled state to its unfurled state.

The ends of the actuator at the retaining rings 22a and 22b remain fixed to the catheter 20. Thus, they do not deform during actuation. Since the actuator begins as a furled structure, its so-called pregnant shape may exist as an unstable buckling mode. This instability, upon actuation, may produce a large-scale motion of the microneedle approximately perpendicular to the central axis of the actuator body, causing a rapid puncture of the body lumen wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle aperture, in fact, travels with such force that it can enter body lumen tissue 32b as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle may have an overall length of between about 200 and 3,000 microns (μm). The interior cross-sectional dimension of the shaft 14b and supply tube 14d may be on the order of 20 to 250 μm, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 μm. The diameter of the delivery tube for the activating fluid may be about 100 μm. The catheter size may be between 1.5 and 15 French (Fr).

Variations of the invention include a multiple-buckling actuator with a single supply tube for the activating fluid. The multiple-buckling actuator includes multiple needles that can be inserted into or through a lumen wall for providing injection at different locations or times.

Figure 4:
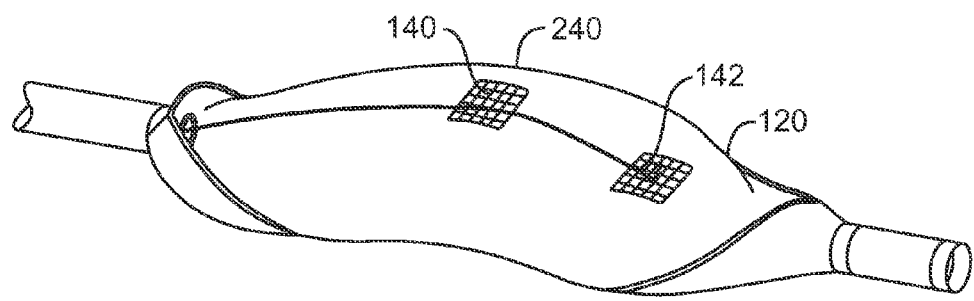
FIG. 4 is a schematic, perspective view of another embodiment of an intraluminal injection catheter useful in the methods of the present invention.

For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
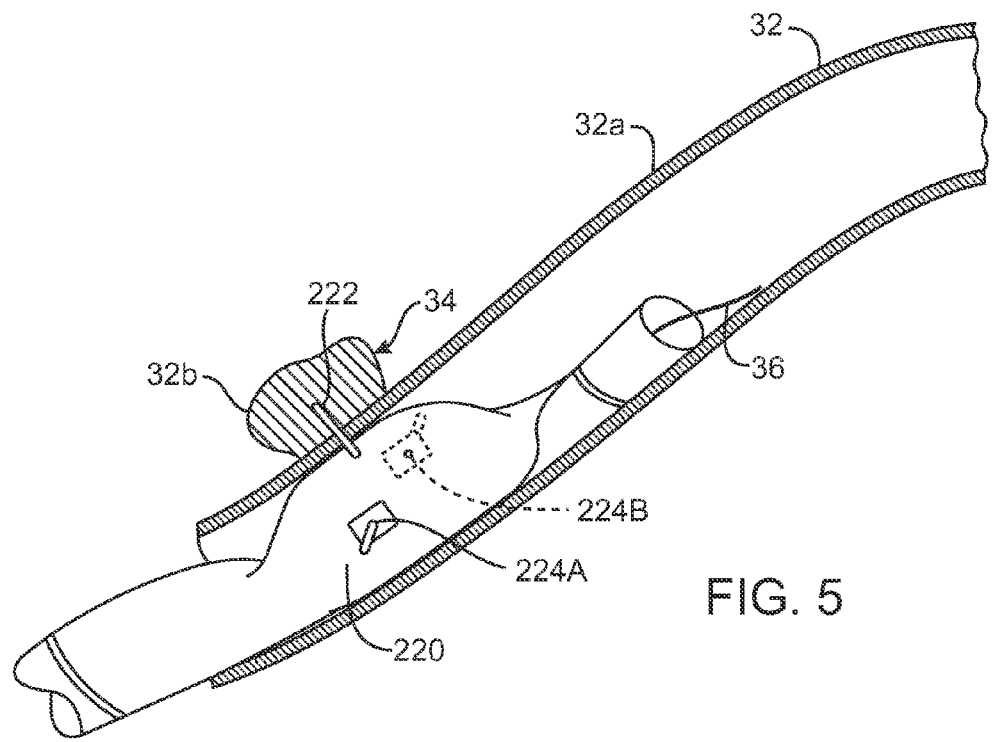
FIG. 5 is a schematic, perspective view of still another embodiment of an intraluminal injection catheter useful in the methods of the present invention, as inserted into one of a patient's body lumens.

Also, as shown in FIG. 5, an actuator 220 could be constructed such that its needles 222 and 224A move in different directions. As shown, upon actuation, the needles move at angle of approximately 90° to each other to puncture different parts of a lumen wall. A needle 224B (as shown in phantom) could alternatively be arranged to move at angle of about 180° to the needle 224A.

The above catheter designs and variations thereon, are described in published U.S. Patent Application Nos. 2003/005546 and 2003/0055400, the full disclosures of which are incorporated herein by reference. Co-pending application Ser. No. 10/350,314, assigned to the assignee of the present application, describes the ability of substances delivered by direct injection into the adventitial and pericardial tissues of the heart to rapidly and evenly distribute within the heart tissues, even to locations remote from the site of injection. The full disclosure of that co-pending application is also incorporated herein by reference. An alternative needle catheter design suitable for delivering the therapeutic or diagnostic agents of the present invention will be described below. That particular catheter design is described and claimed in co-pending application Ser. No. 10/397,700, filed on Mar. 19, 2003, the full disclosure of which is incorporated herein by reference.

Figure 6:
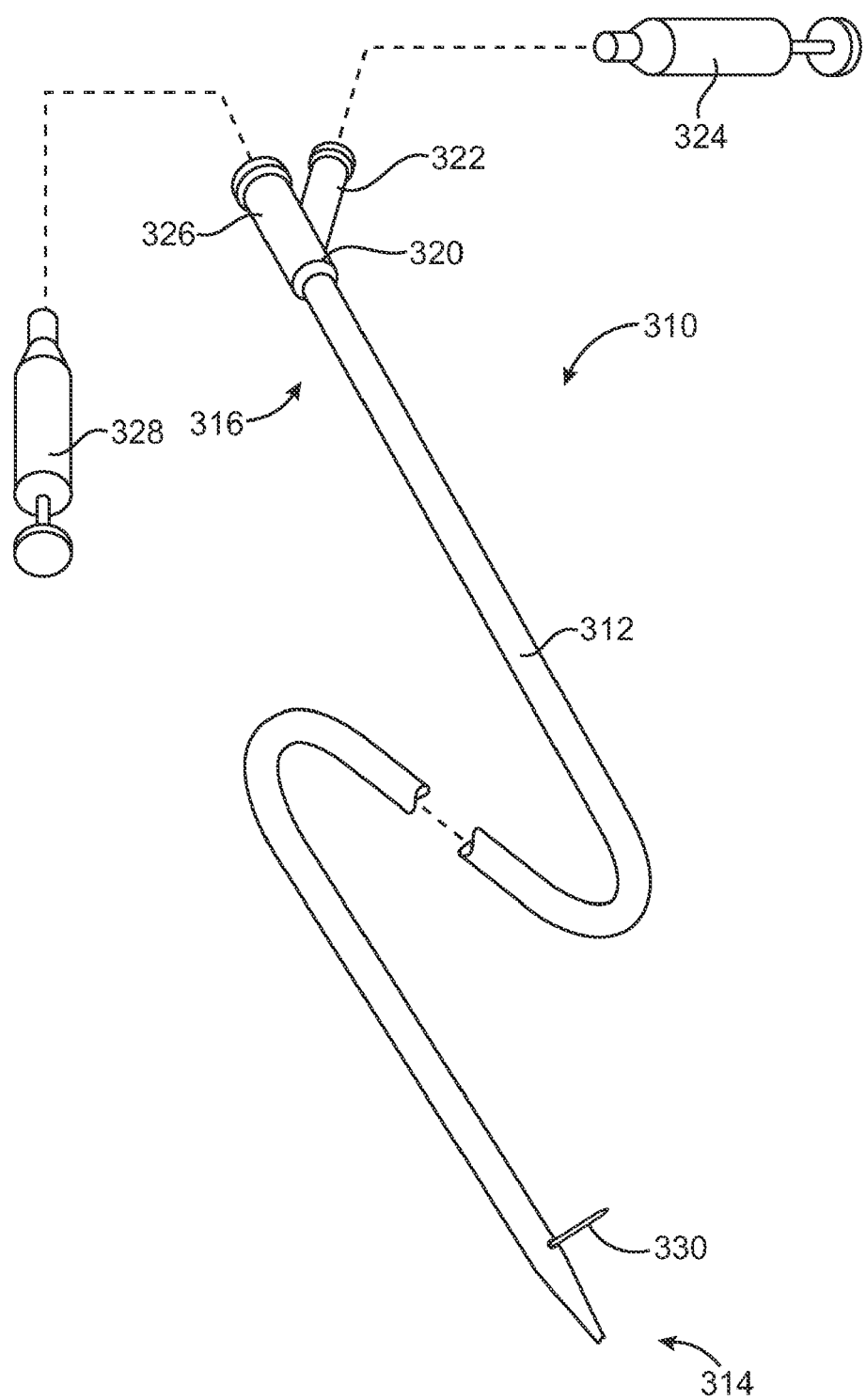
FIG. 6 is a perspective view of a needle injection catheter useful in the methods and systems of the present invention.

Referring now to FIG. 6, a needle injection catheter 310 constructed in accordance with the principles of the present invention comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present invention. A two-port hub 320 is attached to the proximal end 316 of the catheter body 312 and includes a first port 322 for delivery of a hydraulic fluid, e.g., using a syringe 324, and a second port 326 for delivering the pharmaceutical agent, e.g., using a syringe 328. A reciprocatable, deflectable needle 330 is mounted near the distal end of the catheter body 312 and is shown in its laterally advanced configuration in FIG. 6.

Figure 7:
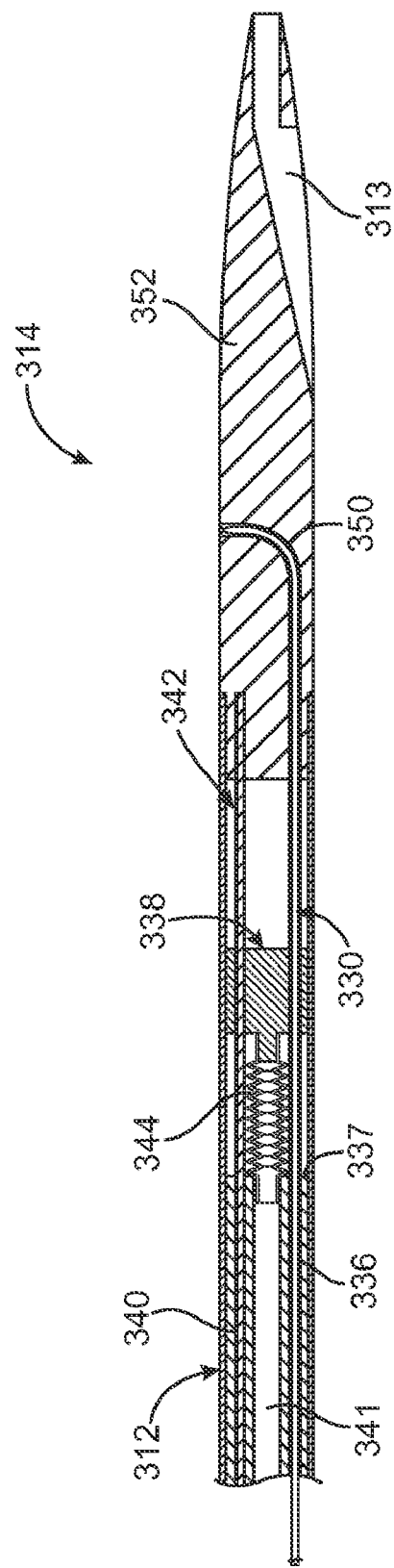
FIG. 7 is a cross-sectional view of the catheter FIG. 6 shown with the injection needle in a refracted configuration.

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 8:
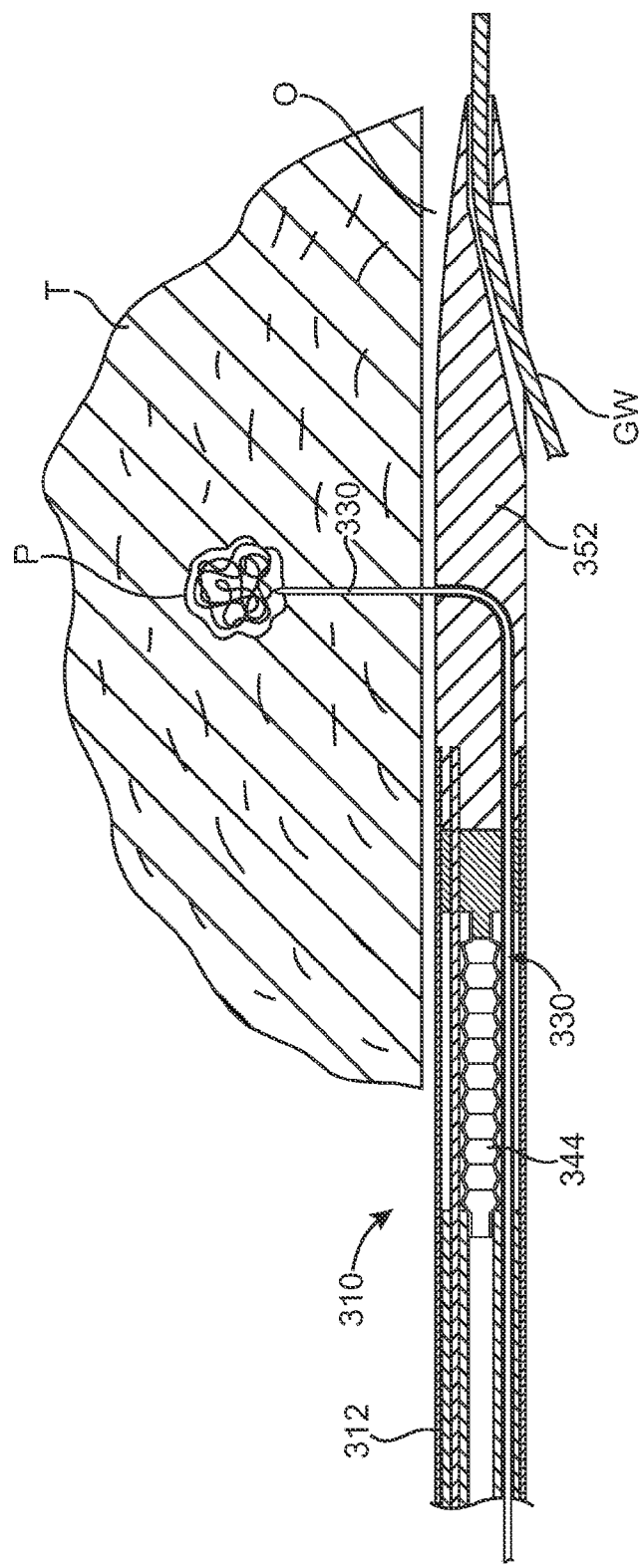
FIG. 8 is a cross-sectional view similar to FIG. 7, shown with the injection needle laterally advanced into luminal tissue for the delivery of therapeutic or diagnostic agents according to the present invention.

As can be seen in FIG. 8, the catheter 310 may be positioned in a coronary blood vessel BV, over a guide wire GW in a conventional manner. Distal advancement of the piston 338 causes the needle 330 to advance into luminal tissue T adjacent to the catheter when it is present in the blood vessel. The therapeutic or diagnostic agents may then be introduced through the port 326 using syringe 328 in order to introduce a plume P of agent in the cardiac tissue, as illustrated in FIG. 8. The plume P will be within or adjacent to the region of tissue damage as described above.

The needle 330 may extend the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing by parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

Figure 9A:
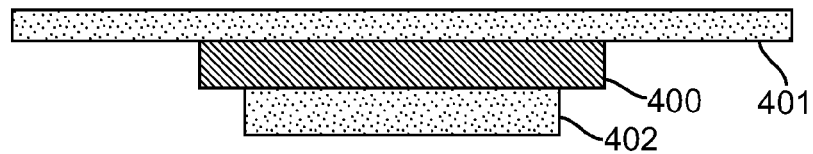
FIGS. 9A-9E are cross-sectional views of an exemplary fabrication process employed to create a free-standing low-modulus patch within a higher modulus anchor, framework or substrate.

FIGS. 9A-9E illustrate an exemplary process for fabricating a dual modulus balloon structure or anchored membrane structure in accordance with the principles of the present invention. The first step of the fabrication process is seen in FIG. 9A, in which a low modulus "patch", or membrane, material 400 is layered between removable (e.g. dissolvable) substrates 401 and 402. The substrate 401 covers one entire face of the patch 400, while the substrate 402 covers only a portion of the opposite face, leaving an exposed edge or border region about the periphery.

Figure 9B:
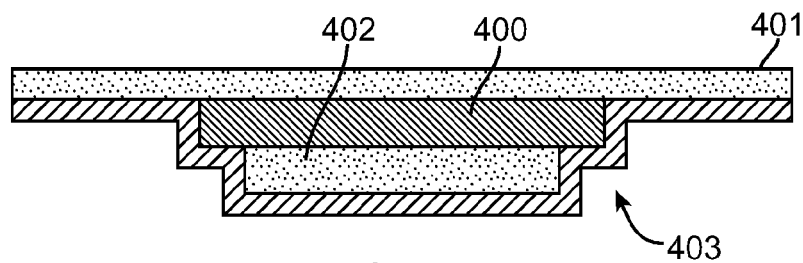

In FIG. 9B, a layer of a "flexible but relatively non-distensible" material 403 is deposited onto one side of the sandwich structure from FIG. 9A to provide a frame to which the low-modulus patch is attached. This material may be, for example, parylene N, C, or D, though it can be one of many other polymers or metals. When the flexible but relatively non-distensible material is parylene and the patch material is a silicone or siloxane polymer, a chemomechanical bond is formed between the layers, creating a strong and leak-free joint between the two materials. The joint formed between the two materials usually has a peel strength or interfacial strength of at least 0.05 N/mm$^2$, typically at least 0.1 N/mm$^2$, and often at least 0.2 N/mm$^2$.

Figure 9C:
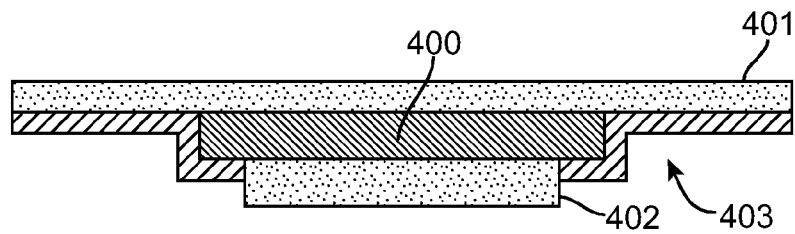
Figure 9D:
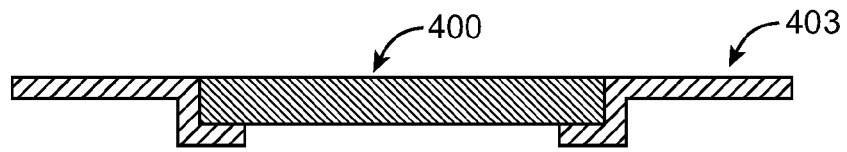

In FIG. 9C, the "flexible but relatively non-distensible" frame or anchor material 403 has been trimmed or etched to expose the substrate material 402 so that it can be removed. Materials 401 and 402 may be dissolvable polymers that can be removed by one of many chemical solvents. In FIG. 9D, the materials 401 and 402 have been removed by dissolution, leaving materials 400 and 403 joined edge-to-edge to form the low modulus, or elastomeric, patch 400 within a frame of generally flexible but relatively non-distensible material 403.

Figure 9E:
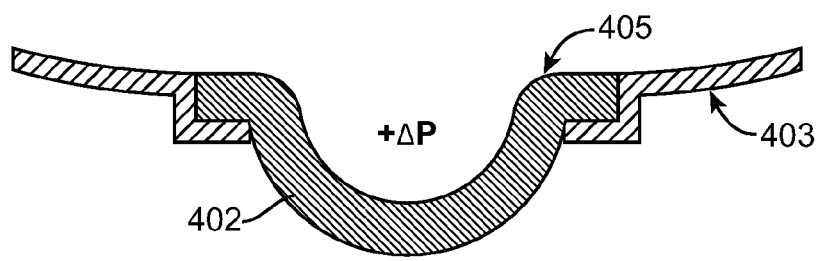

As shown in FIG. 9E, when positive pressure $+\Delta P$ is applied to one side 405 of the structure, the non-distensible frame 403 deforms only slightly, while the elastomeric patch 400 deforms much more. The low modulus material may have a material modulus which is always lower than that of the high modulus material and is typically in the range from 0.1 to 1,000 MPa, more typically in the range from 1 to 250 MPa. The high modulus material may have a material modulus in the range from 1 to 50,000 MPa, more typically in the range from 10 to 10,000 MPa. The material thicknesses may range in both cases from approximately 1 micron to several millimeters, depending on the ultimate size of the intended product. For the treatment of most body lumens, the thicknesses of both material layers 402 and 403 are in the range from 10 microns to 2 mm.

Referring to FIGS. 10A-10D, the elastomeric patch of FIGS. 9A-9D is integrated into the intraluminal catheter of FIG. 1-5. In FIG. 10A-D, the progressive pressurization of such a structure is displayed in order of increasing pressure. In FIG. 10A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Actuation of the balloon 12 occurs with positive pressurization. In FIG. 10B, pressure $(+\Delta P_1)$ is added, which begins to deform the flexible but relatively non-distensible structure, causing the balloon involution to begin its reversal toward the lower energy state of a round pressure vessel. At higher pressure $+\Delta P_2$ in FIG. 10C, the flexible but relatively non-distensible balloon material has reached its rounded shape and the elastomeric patch has begun to stretch. Finally, in FIG. 10D at still higher pressure $+\Delta P_3$, the elastomeric patch has stretched out to accommodate the full lumen diameter, providing an opposing force to the needle tip and sliding the needle through the lumen wall and into the adventitia. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure $+\Delta P$ useful to cause actuation of the balloon is typically in the range from 0.1 atmospheres to 20 atmospheres, more typically in the range from 0.5 to 20 atmospheres, and often in the range from 1 to 10 atmospheres.

Figure 11A:
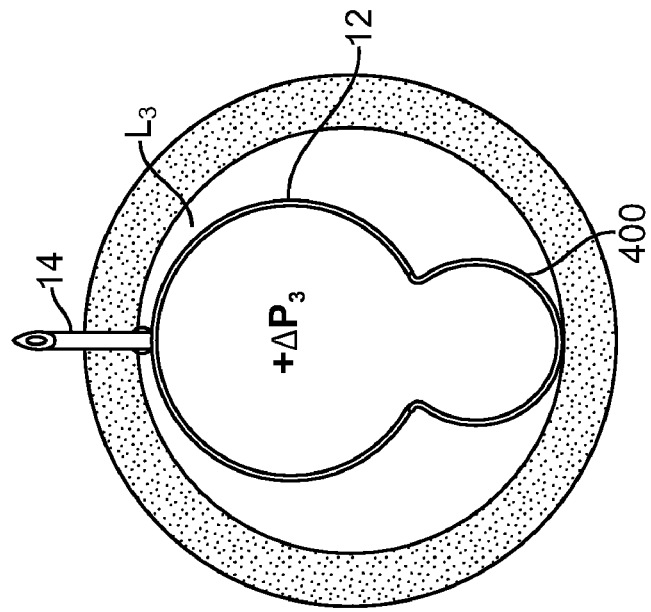
FIGS. 11A-11C are cross-sectional views of the inflated intraluminal injection catheter useful in the methods of the present invention, illustrating the ability to treat multiple lumen diameters.
Figure 11B:
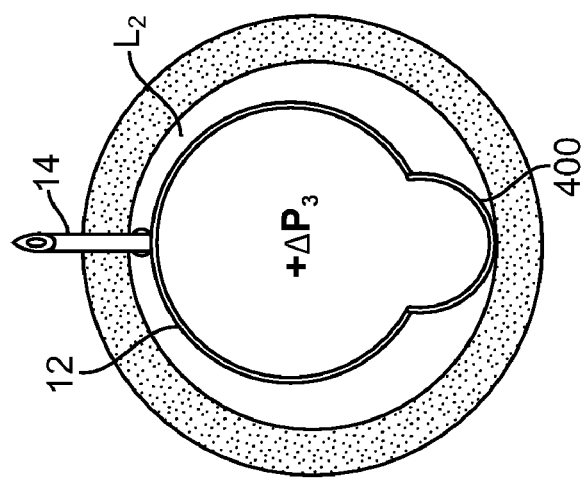
Figure 11C:
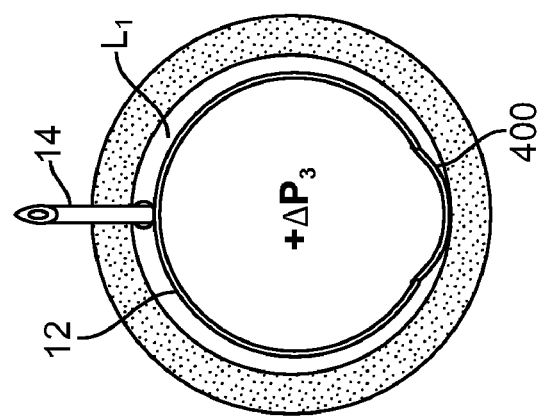

As illustrated in FIGS. 11A-11C, the dual modulus structure formed herein provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure $+\Delta P_3$ in three different lumen diameters in FIGS. 11A, 11B, and 11C. for the progressively larger inflation of patch 400 provides optimal apposition of the needle through the vessel wall regardless of diameter. Thus, a variable diameter system is created in which the same catheter may be employed in lumens throughout the body that are within a range of diameters. This is useful because most medical products are limited to very tight constraints (typically within 0.5 mm) in which lumens they may be used. A system as described in this invention may accommodate several millimeters of variability in the luminal diameters for which they are useful.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for deploying a tool in a body lumen, said method comprising:
   introducing the tool into the body lumen;
   inflating an actuator to advance the tool within the body lumen, wherein the actuator is inflated to a pressure below a threshold pressure to advance the tool by a fixed distance determined by a flexible but relatively non-distensible section of the actuator; and
   inflating the actuator to further advance the tool within the body lumen, wherein the actuator is inflated to a pressure above the threshold pressure to allow expansion of an elastomeric region of the actuator which was not significantly inflated at pressures below the threshold pressure;
   wherein inflating the actuator to the pressure opens an involuted section of the actuator to advance the tool by said fixed distance;
   wherein the involuted section is formed from a non-distensible material which limits the distance the needle can travel.

2. A method as in claim 1, wherein introducing comprise advancing a catheter carrying the tool into a blood vessel.

3. A method as in claim 2, the tool is a needle and inflating the actuator advances the needle into a wall of the blood vessel.

4. A method as in claim 3, wherein the actuator further comprise a section formed from an elastomeric material which inflates at pressures above the threshold pressure to advance to needle beyond the fixed distance.

5. A method as in claim 3, wherein the elastomeric material is disposed on a side of the actuator opposite to the involuted section so that distension of the elastomeric material will push against the blood vessel wall to advance the needle.

* * * * *